United States Patent
Schoenberg

(10) Patent No.: US 8,463,620 B2
(45) Date of Patent: Jun. 11, 2013

(54) CONNECTING CONSUMERS WITH SERVICE PROVIDERS

(75) Inventor: Roy Schoenberg, Boston, MA (US)

(73) Assignee: American Well Corporation, Boston, MA (US)

( * ) Notice: Subject to any disclaimer, the term of this patent is extended or adjusted under 35 U.S.C. 154(b) by 352 days.

(21) Appl. No.: 12/633,115

(22) Filed: Dec. 8, 2009

(65) Prior Publication Data

US 2011/0010197 A1    Jan. 13, 2011

Related U.S. Application Data

(60) Provisional application No. 61/223,901, filed on Jul. 8, 2009.

(51) Int. Cl.
     *G06Q 10/00*      (2012.01)
     *G06Q 50/00*      (2012.01)

(52) U.S. Cl.
     USPC .................................. 705/2; 705/3; 705/7.13

(58) Field of Classification Search
     USPC ................................................. 705/2–3, 7.13
     See application file for complete search history.

(56) References Cited

U.S. PATENT DOCUMENTS

| | | | |
|---|---|---|---|
| 5,801,755 A | 9/1998 | Echerer | |
| 5,911,687 A | 6/1999 | Sato et al. | |
| 6,223,165 B1 | 4/2001 | Lauffer | |
| 6,519,570 B1 | 2/2003 | Faber et al. | |
| 7,308,422 B1 | 12/2007 | Faber et al. | |
| 7,412,396 B1 | 8/2008 | Haq | |
| 7,590,550 B2 | 9/2009 | Schoenberg | |
| 2001/0051765 A1 | 12/2001 | Walker et al. | |
| 2002/0010608 A1 | 1/2002 | Faber et al. | |
| 2002/0165732 A1 | 11/2002 | Ezzeddine et al. | |
| 2003/0023508 A1 | 1/2003 | Deep | |
| 2003/0069752 A1 | 4/2003 | LeDain et al. | |
| 2003/0093294 A1 | 5/2003 | Passantino | |
| 2003/0144580 A1 | 7/2003 | Iliff | |
| 2003/0195838 A1 | 10/2003 | Henley | |
| 2004/0019579 A1 | 1/2004 | Herz et al. | |
| 2004/0093290 A1* | 5/2004 | Doss et al. ...................... | 705/35 |
| 2004/0111297 A1 | 6/2004 | Schoenberg | |
| 2004/0111298 A1 | 6/2004 | Schoenberg | |

(Continued)

FOREIGN PATENT DOCUMENTS

| | | |
|---|---|---|
| WO | WO 00/57326 | 9/2000 |
| WO | WO 01/22718 | 3/2001 |
| WO | WO 2008/141283 A2 | 11/2008 |

OTHER PUBLICATIONS

U.S. Appl. No. 12/140,760, filed Jun. 17, 2008, Roy Schoenberg.

(Continued)

*Primary Examiner* — Lena Najarian
*Assistant Examiner* — Minnah Seoh
(74) *Attorney, Agent, or Firm* — Fish & Richardson P.C.

(57) ABSTRACT

A request to generate a medical service team for a particular consumer of medical services is received and records including names of one or more medical service providers associated with providing a medical service to the consumer of medical services are retrieved from a data repository. An electronic invitation to join the medical service team associated with providing medical services to the consumer of medical services is sent and responses to the invitation are received. A listing of medical service team members is generated from the responses and the records.

32 Claims, 11 Drawing Sheets

U.S. PATENT DOCUMENTS

| | | | |
|---|---|---|---|
| 2004/0111622 A1 | 6/2004 | Schoenberg | |
| 2004/0152952 A1 | 8/2004 | Gotlib et al. | |
| 2004/0153343 A1 | 8/2004 | Gotlib et al. | |
| 2004/0181430 A1 | 9/2004 | Fotsch et al. | |
| 2005/0060198 A1* | 3/2005 | Bayne | 705/2 |
| 2005/0065813 A1 | 3/2005 | Mishelevich et al. | |
| 2005/0108052 A1 | 5/2005 | Omaboe | |
| 2005/0125252 A1 | 6/2005 | Schoenberg | |
| 2005/0125254 A1 | 6/2005 | Schoenberg | |
| 2005/0125435 A1 | 6/2005 | Schoenberg | |
| 2005/0125446 A1 | 6/2005 | Schoenberg | |
| 2005/0125487 A1 | 6/2005 | O'Connor et al. | |
| 2005/0182743 A1 | 8/2005 | Koenig | |
| 2005/0234739 A1 | 10/2005 | Schoenberg | |
| 2005/0234745 A1 | 10/2005 | Schoenberg | |
| 2005/0288965 A1 | 12/2005 | Van Eaton et al. | |
| 2006/0106644 A1 | 5/2006 | Koo et al. | |
| 2006/0116900 A1 | 6/2006 | Jensen | |
| 2006/0122850 A1 | 6/2006 | Ward et al. | |
| 2006/0136264 A1 | 6/2006 | Eaton et al. | |
| 2006/0161457 A1 | 7/2006 | Rapaport et al. | |
| 2006/0247968 A1 | 11/2006 | Kadry | |
| 2007/0088580 A1 | 4/2007 | Richards, Jr. | |
| 2007/0150372 A1 | 6/2007 | Schoenberg | |
| 2007/0299316 A1 | 12/2007 | Haslehurst et al. | |
| 2008/0065414 A1 | 3/2008 | Schoenberg | |
| 2008/0065726 A1 | 3/2008 | Schoenberg | |
| 2008/0133511 A1 | 6/2008 | Schoenberg | |
| 2008/0147472 A1* | 6/2008 | Hitz | 705/9 |
| 2009/0063188 A1 | 3/2009 | Schoenberg | |
| 2009/0089074 A1 | 4/2009 | Schoenberg | |
| 2009/0089084 A1 | 4/2009 | Schoenberg | |
| 2009/0089085 A1 | 4/2009 | Schoenberg | |
| 2009/0089086 A1 | 4/2009 | Schoenberg | |
| 2009/0089088 A1 | 4/2009 | Schoenberg | |
| 2009/0089090 A1 | 4/2009 | Schoenberg | |
| 2009/0089096 A1 | 4/2009 | Schoenberg | |
| 2009/0089097 A1 | 4/2009 | Schoenberg | |
| 2009/0089098 A1 | 4/2009 | Schoenberg | |
| 2009/0089147 A1 | 4/2009 | Schoenberg | |
| 2009/0112623 A1 | 4/2009 | Schoenberg | |
| 2009/0150252 A1 | 6/2009 | Schoenberg | |
| 2009/0254361 A1 | 10/2009 | Schoenberg | |
| 2009/0262919 A1 | 10/2009 | Schoenberg | |
| 2010/0325214 A1* | 12/2010 | Gupta | 709/206 |

OTHER PUBLICATIONS

U.S. Appl. No. 12/396,406, filed Mar. 2, 2009, Roy Schoenberg.
U.S. Appl. No. 12/486,637, filed Jun. 17, 2009, Roy Schoenberg.
U.S. Appl. No. 12/348,642, Jan. 5, 2009, Schoenberg.
U.S. Appl. No. 12/270,224, Nov. 13, 2008, Schoenberg.

* cited by examiner

Online Care

Home | My Patients

John Alan | My Current Availability: Available (Web & Phone) | My Account | System Check | Log Out My History | Message Center | Provider Reference | Help

Patient Profile —42

Lee Rodriquez     Male, Age: 29     PCP: Otto Matic, Internist

| Recent Conditions | Last Diagnosis |
|---|---|
| Pneumonia due to parainfluenza virus | 7/2/2009 |
| Diabetes -- Type II (Adult Onset) | 6/25/2009 |
| Influenza | 5/7/2009 |
| Acute Bronchitis | 4/26/2009 |
| Skin rash on the hand and leg | 7/16/2009 |

View Full Health Summary >

| Recent Medications | Date | Status |
|---|---|---|
| Cyclobenzaprine | 6/25/2009 | Prescribed |
| Ativan | 4/15/2009 | Filled |
| Ibuprofen | 5/25/2009 | Prescribed |
| Codeine | 3/22/2009 | Filled |

Health History | Insight

Attach a File | ⊕ Consult a Specialist | ✉ Secure Message | ⊕ Create Medical Home —44

View: [All Entries ▼]   Sort By: [Type ▼]

| | | |
|---|---|---|
| 📄 Health Summary | | |
| 🔷 HealthVault Record: Conditions | | |
| 🔷 HealthVault Record: Medications | | |
| 🔷 HealthVault Record: Procedures | | |
| 📊 Tracker: Blood Glucose | | |
| 📊 Tracker: Body Weight | | |
| ⊕ Conversation with John Alan, Allergist | 4/19/2009 | |
| ⊕ Conversation with Otto Matic, Internist | 4/12/2009 | |
| ⊕ Conversation with John Simpson, Podiatrist | 3/12/2009 | |
| ⊕ Conversation with Jamie Baker, Oncologist | 2/2/2009 | |
| 📄 Assessment Report -- Lorem Ipsum Dolor sit Amet | 5/21/2009 | |
| 📄 Assessment Report -- Lorem Ipsum Dolor sit Amet | 3/21/2009 | X Remove |
| 📄 Imaging - X - Ray: WorthingtonA9327.jpg<br>UT enim as minum venea, quis nostrum exert reprehendint in voluptate velit aees cillum delor eu forgait nulla paniatur sint occaecat cupidar. [Added by Otto matic] | 4/12/2009 | |
| 📄 Lab Results -- Lorem Ipsum: WorthingtonA9328.jpg<br>UT enim as minum venea, quis nostrum exert reprehendint in voluptate velit aees cillum delor [Added by Otto Matic] | 4/12/2009 | X Remove |

Results 1 - 15     PREVIOUS | NEXT

Online Care

Home | My Patients | My History | Message Center | Provider Reference

Maria Lopez | My Current Availability: Available (Web & Phone) | My Account | Test System | Log Out

Welcome to Online Care

My Agenda

My Current Availability: Available (Web & Phone) ▼

SEPTEMBER 2009
| S | M | T | W | T | F | S |
|---|---|---|---|---|---|---|
| 29 | 30 | 1 | 2 | 3 | 4 | 5 |
| 6 | 7 | 8 | 9 | 10 | 11 | 12 |
| 13 | 14 | 15 | 16 | 17 | 18 | 19 |
| 20 | 21 | 22 | 23 | 24 | 25 | 26 |
| 27 | 28 | 29 | 30 | 21 | 1 | 2 |

Upcoming Appointments
- 10:15 AM EDT 9/23/2009
- 10:30 AM EDT 9/23/2009
- 10:45 AM EDT 9/23/2009
- 2:00 PM EDT 9/26/2009
- 3:00 PM EDT 9/28/2009

View All >

Waiting Room
There are 3 Members Currently in your Waiting Room

---

Account Snapshot

THIS MONTH (pie chart: 12, 3, 1)

CONVERSATONS
- ☐ Complete
- ☐ Incomplete
- ☐ Cancelled

CONVERSATIONS THIS YEAR = 78
Consumer Rating: ☆☆☆☆☆
View Earnings Activity

My History

| | Date | Member | |
|---|---|---|---|
| | 3:20 PM EDT 9/5/09 | Betty Peterson | Complete Wrap-Up |
| | 3:00 PM EDT 9/5/09 | John Franklin | Complete Wrap-Up |
| | 2:40 PM EDT 9/5/09 | Timothy Longfellow | Complete Wrap-Up |
| | 10:15 AM EDT 9/4/09 | Sean Brady | View Report |
| | 10:00 AM EDT 9/4/09 | Ryan White | View Report |

View All >

---

Tools — 218

My Patients   Add Patient
First Name: [    ]
Last Name: [    ]
Find
View All Patients >

Message Center — 220
4 New Messages!
1 New Invitation!

Provider Reference
Browse our extensive collection of medical reference material.

Current Demand
Estimated for your specialty as of 4:00 pm EDT
LOW — MED — HIGH

Online Care

John Alan | My Current Availability: Available (Web & Phone) | My Account | System Check | Log Out

Home | My Patients | My History | Message Center | Provider Reference | Help

My Patients

+ Add Patient

First Name: [ ]  Last Name: [ ]  Relationship: [ ▼ ]  Sort By: [Alphabetical ▼]  [Apply]

Relationship (?) —264

| | Name | D.O.B | Relationship |  |
|---|---|---|---|---|
| | Karen L. Worthington | 7/1/1967 | Medical Home Manager —266 | Consult a Specialist |
| | Jake N. Myers | 3/16/1963 | Medical Home Manager —266 | Consult a Specialist |
| | Robert Y. Wilson | 12/16/1979 | Medical Home Team Member —268 | Consult a Specialist |
| | Karen K. White | 4/7/1959 | Medical Home Team Member —268 | Consult a Specialist |
| | Lisa M. Sanders | 10/28/1952 | Medical Home Team Member —268 | Consult a Specialist |
| | Katherine L. Smith | 10/1/1970 | Treating Physician | Consult a Specialist |
| | Steven L. Lee | 9/18/1984 | Treating Physician | Consult a Specialist |
| | Donna K. Adams | 4/1/1979 | Treating Physician | Consult a Specialist |
| | Amy T. Perez | 12/13/1975 | Online care Physician | Consult a Specialist |
| | Lee B. Rodriguez | 6/2/1957 | Online care Physician | Consult a Specialist |
| | John D. Carter | 8/17/1966 | Online care Physician | Consult a Specialist |
| | James K. Long | 4/11/1960 | Online care Physician | Consult a Specialist |
| | Connie R. Roberts | 11/11/1948 | -- | Consult a Specialist |
| | Kim L. Baily | 9/28/1967 | | Consult a Specialist |
| | John R. Smith | 5/30/1939 | -- | Consult a Specialist |

Patients 1-15 of 45                                                                 PREVIOUS | NEXT

260 →

262

CONNECTING CONSUMERS WITH SERVICE PROVIDERS

CLAIM OF PRIORITY

This application claims priority under 35 U.S.C. §119(e) to provisional U.S. Patent Application 61/223,901, filed on Jul. 8, 2009, the entire contents of which are hereby incorporated by reference.

BACKGROUND

The present invention is directed to connecting consumers with service providers.

Systems have been developed to connect consumers and their providers over the Internet and the World Wide Web. Some systems use e-mail messaging and web-based forms to increase the level of connectivity between a member of a health plan and his assigned health care provider. The consumer sends an e-mail or goes to a website that generates and sends a message (typically an e-mail or an e-mail type message) to a local provider.

These types of services have been broadly referred to as "e-visits." While generally viewed as an addition to the spectrum of services that may be desired by consumers, the benefits of such services are not clear. One of the concerns associated with offering additional communication channels, such as e-mail, is that it can result in over consumption of services, rather than provide for better coordination.

Another system is a brokerage type of system as described in my issued U.S. Pat. No. 7,590,550, which is incorporated herein by reference.

SUMMARY

In general, in one aspect, a request to generate a medical service team for a particular consumer of medical services is received and records including names of one or more medical service providers associated with providing a medical service to the consumer of medical services are retrieved from a data repository. An electronic invitation to join the medical service team associated with providing medical services to the consumer of medical services is sent and responses to the invitation are received. A listing of medical service team members is generated from the responses and the records.

Implementations may include one or more of the following features. An instruction to send the electronic invitation to one or more selected service providers is received from one of the medical service team members. The listing of medical service team members is updated with names of one or more service providers accepting the electronic invitation. A message including names of one or more other medical service team members to be removed from the listing of medical service team members is received from one of the medical service team members and the received names of the one or more other medical service team members are removed from the listing of medical service team members.

Implementations may also include one or more of the following features. Status data regarding present availability of the one or more medical service providers on the listing of medical service team members is retrieved from a data repository and a user interface is generated. The user interface renders one or more visual representations of the one or more medical service providers with an indication of the present availability status of the one or more medical service providers juxtaposed to the one or more visual representations. Medical specialty data is also retrieved from the data repository, with the medical specialty data including the one or more medical service providers on the listing of medical service team members. A user interface is generated that renders one or more visual representations of the one or more medical service providers with medical specialty data of the medical service providers juxtaposed to the one or more visual representations. A real-time communication channel is established between one of the medical service team members and one or more other, different medical service teams members. A real-time communication channel is established between one or more of the medical service team members and the consumer of medical services.

In general, in one aspect, a computer-implemented method comprises generating by a computer a first graphical user interface, the first graphical user interface when displayed on a display device, rendering: a first visual representation corresponding to at least one or more medical service providers associated with a consumer's medical service team; a second visual representation corresponding to one or more prior communications between a consumer of services and the one or more medical service providers associated with the consumer's medical service team; and a first link that when selected causes a computing device associated with the display device on which the first graphical user interface is rendered to send a message to a brokerage system to establish a real-time communication channel between one of the one or more medical service providers associated with the consumer's medical service team and another, different one of the one or more medical service providers associated with the consumer's medical service team.

Implementations may include one or more of the following features. A visual representation of a timeline indicating, for each of the communications between the consumer of services and a medical service provider, a date of the communication. A third visual representation corresponding to a list of topics posted to a virtual discussion board by one or more of the medical service providers associated with the consumer's medical service team; and a second link that when selected causes the display device to display a second, different graphical user interface including a text box in which a medical service provider enters a topic for discussion.

Implementations may also include one or more of the following features. A fourth visual representation corresponding to a current availability of the one or more medical service providers associated with the consumer's medical service team; and a fifth visual representation including data indicative of medical conditions and medications associated with the consumer of services. A second link that when selected causes the display device to display a second, different graphical user interface including health history information associated with the consumer of services; and a third link that when selected causes the display device to display a third, different graphical user interface including provider decision support information.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIGS. 2, 4, 6A, 6B, 7, 8 and 9 are screen images of graphical user interfaces generated by the brokerage system.

DETAILED DESCRIPTION

Through a brokerage system, a consumer of services engages in a consultation with a service provider, as described in my issued patent, U.S. Pat. No. 7,590,550. Additionally, through the brokerage system, a service provider accesses and views information of other service providers associated with the brokerage system.

Using the brokerage system and its associated services, a service provider assembles a medical services team (referred to herein as a "medical home team"), including a team of one or more other service providers collaborating together to provide a consumer (e.g., a patient) with coordinated health care. The medical home team shares clinical information with each other regarding a consumer, views updates to a consumer's health record and initiates consultations with each other or other service providers not otherwise part of the medical home team. The service provider who assembles the medical home team is referred to as the medical home manager. The other service providers, who were invited by the medical home manager to join the medical home team, are referred to as medical home team members.

Generation of a Medical Home Team

Figure 1:
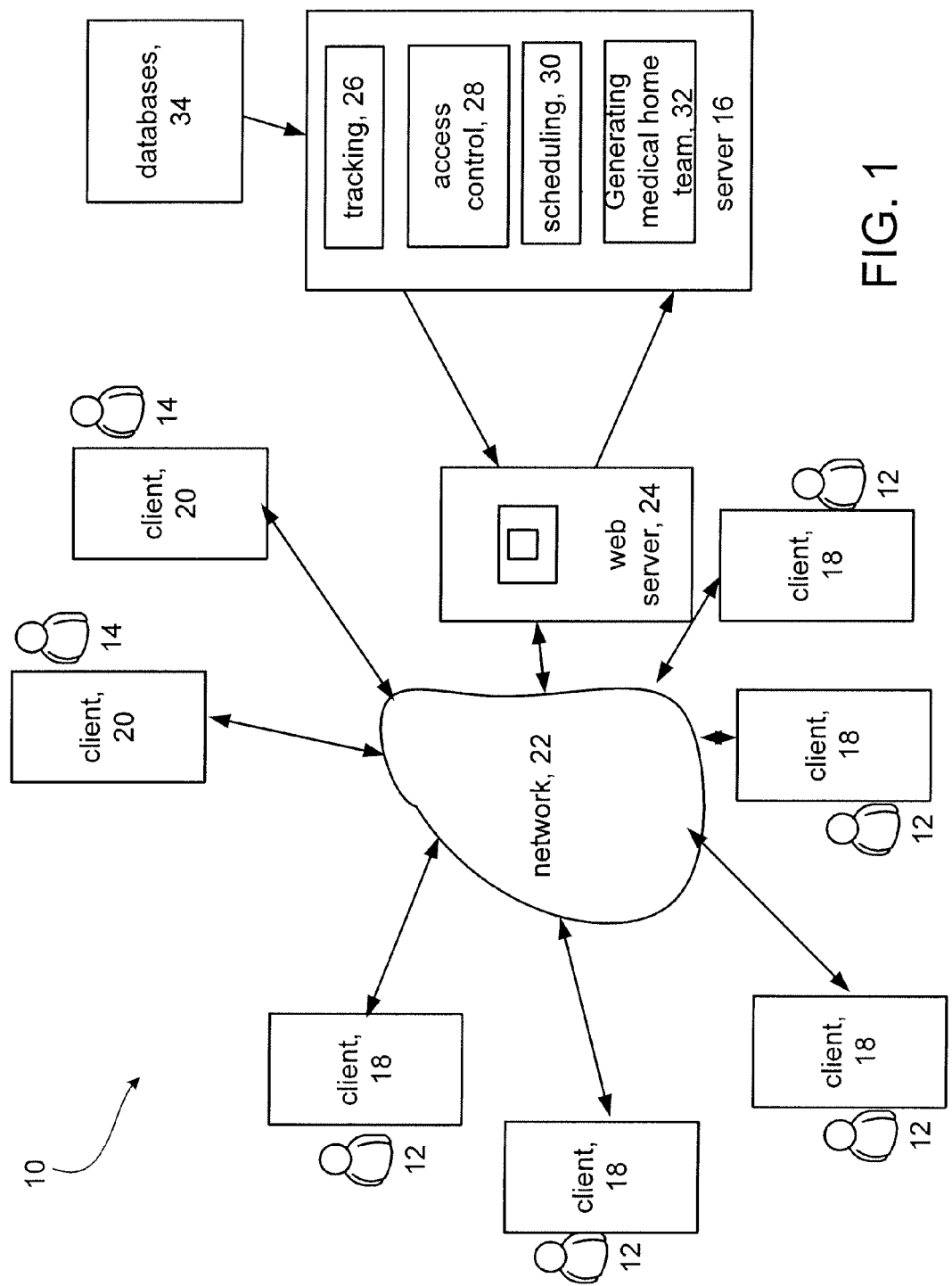
FIG. 1 is a block diagram of a computer-based brokerage system.

Referring to FIG. 1, a brokerage system 10 to provide a brokerage service to connect consumers of services 12 with providers of services 14 is shown. The system 10 includes a computerized system or server 16 for making connections between consumers 12, at client systems 18, and service providers 14, at client systems 20, over a network 22, e.g., the Internet or other types of networks. The computerized system 16 operates as a service running on a web server 24.

The computerized system 16 includes an availability or presence tracking module 26 for tracking the availability of the service providers 14. The computerized system 16 includes an access control facility 28, which manages and controls whether a given consumer 12 has access to the system 16 and what level or scope of access to the features, functions, and services is provided by the system 16. The computerized system 16 also includes one or more processes such as a scheduling module 30. Also included in the computerized system 16 is a process 32 that allows a service provider 14 to generate a medical home team, as described in more detail below. The system 16 accesses one or more databases 34. The components of the system 16 and the web server 24 are integrated or distributed in various combinations as is commonly known in the art.

Using the system 10, a consumer 12 communicates with a provider 14. The consumers 12 and providers 14 connect to the computerized system 16 through a website or other interface on the web server 24 using client devices 18 and 20, respectively. Client devices 18 and 20 include any combination of, e.g., personal digital assistants, land-line telephones, cell phones, computer systems, media-player-type devices, and so forth. The client devices 18 and 20 enable the consumers 12 to input and receive information as well as to communicate via video, audio, and/or text with the providers 14.

Referring to FIG. 2, a graphical user interface 40, generated through the brokerage system 10 and displayed for a service provider 14 on a service provider system 20, includes a consumer's profile 42 and a link 44. Selection of the link 44 allows a service provider 14 to generate a medical home team. The brokerage system 10 lists the service provider 14 who selects the link 44 as the medical home manager. Selection of link 44 results in sending of a message or data from the service provider's system 20 to the server 16 in the brokerage system 10 to generate a medical home team.

Figure 3:
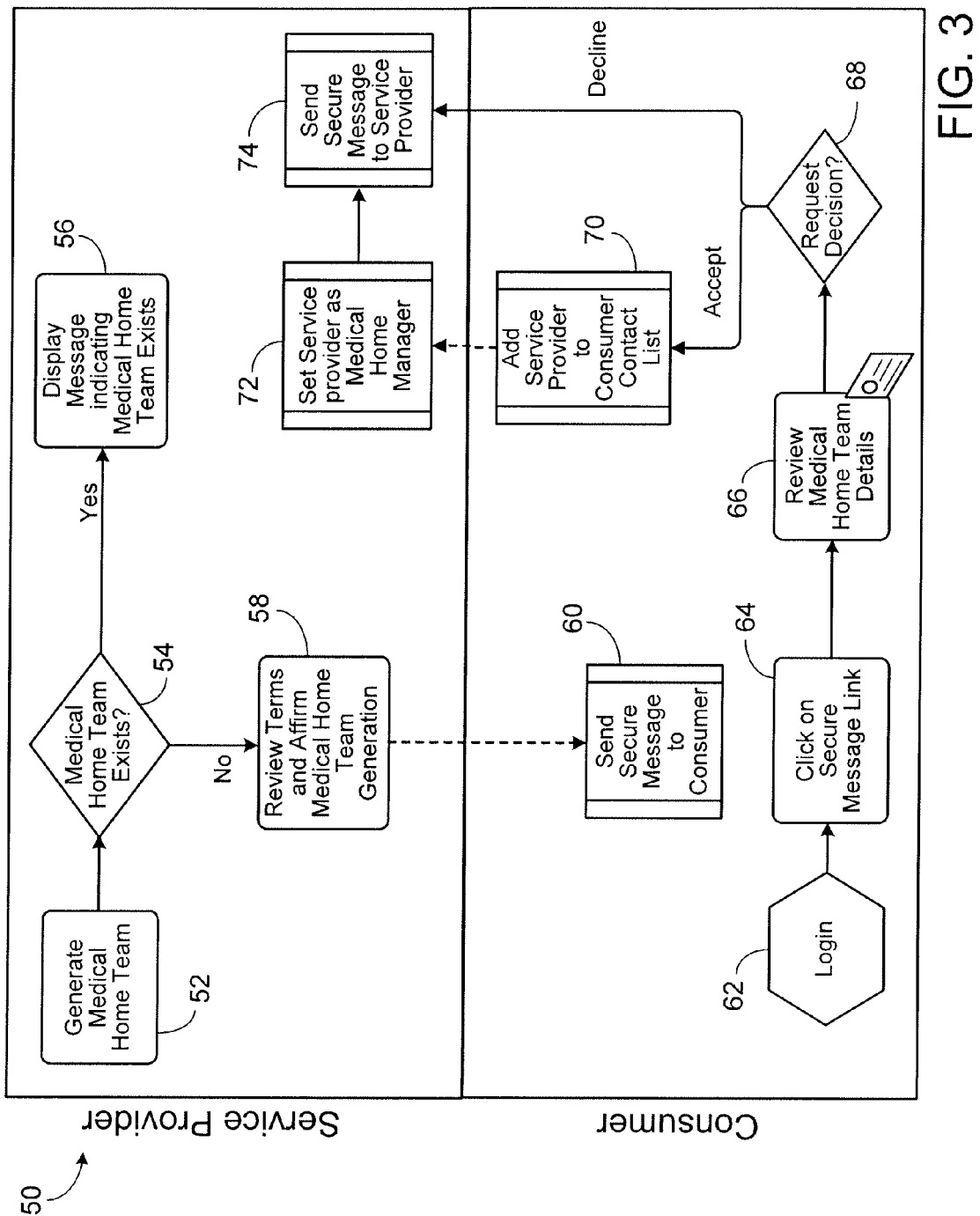
FIGS. 3, 5 and 10 are flow charts of processes executed in the brokerage system.

Referring to FIG. 3, generation 50 of a medical home team is shown. The brokerage system 10 receives 52 a message from a service provider 14 to generate a medical home team. The brokerage system 10 determines 54 whether a medical home team already exists. If a medical home team already exists, a message is displayed 56 to the service provider 14 indicating that a medical home team already exists. If the brokerage system 10 determines that a medical home team does not already exist, then a graphical user interface is displayed 58 that includes the terms and conditions associated with generating a medical home team and prompts the service provider 14 to affirm the service provider's request to generate a medical home team. Upon the service provider's affirmation of the request to generate a medical home team, a secure message is sent 60 to the consumer's electronic mail inbox associated with the brokerage system 10.

The consumer 12 logs 62 into the brokerage system 10 and accesses the secure message including the request to generate a medical home team by clicking 64 on a link associated with the secure message. The consumer 12 reviews 66 the details of the request to generate a medical home team, including the name of the service provider 14 initiating the request, and decides 68 whether to accept or decline the request. If the consumer 12 declines the request, the brokerage system 10 sends 74 a secure message to the service provider 14 initiating the request. The message indicates that the consumer 12 has declined the request to generate a medical home team.

If the consumer 12 accepts the request to generate a medical home team, the service provider 14 is added 70 to the consumer's contact list of service providers and the brokerage system 10 sets 72 the service provider 14 making the request as the medical home manager. The brokerage system 10 sends 74 a secure message, indicating the consumer's acceptance of the request to generate the medical home team, to the service provider 14 initiating the request.

Figure 4:
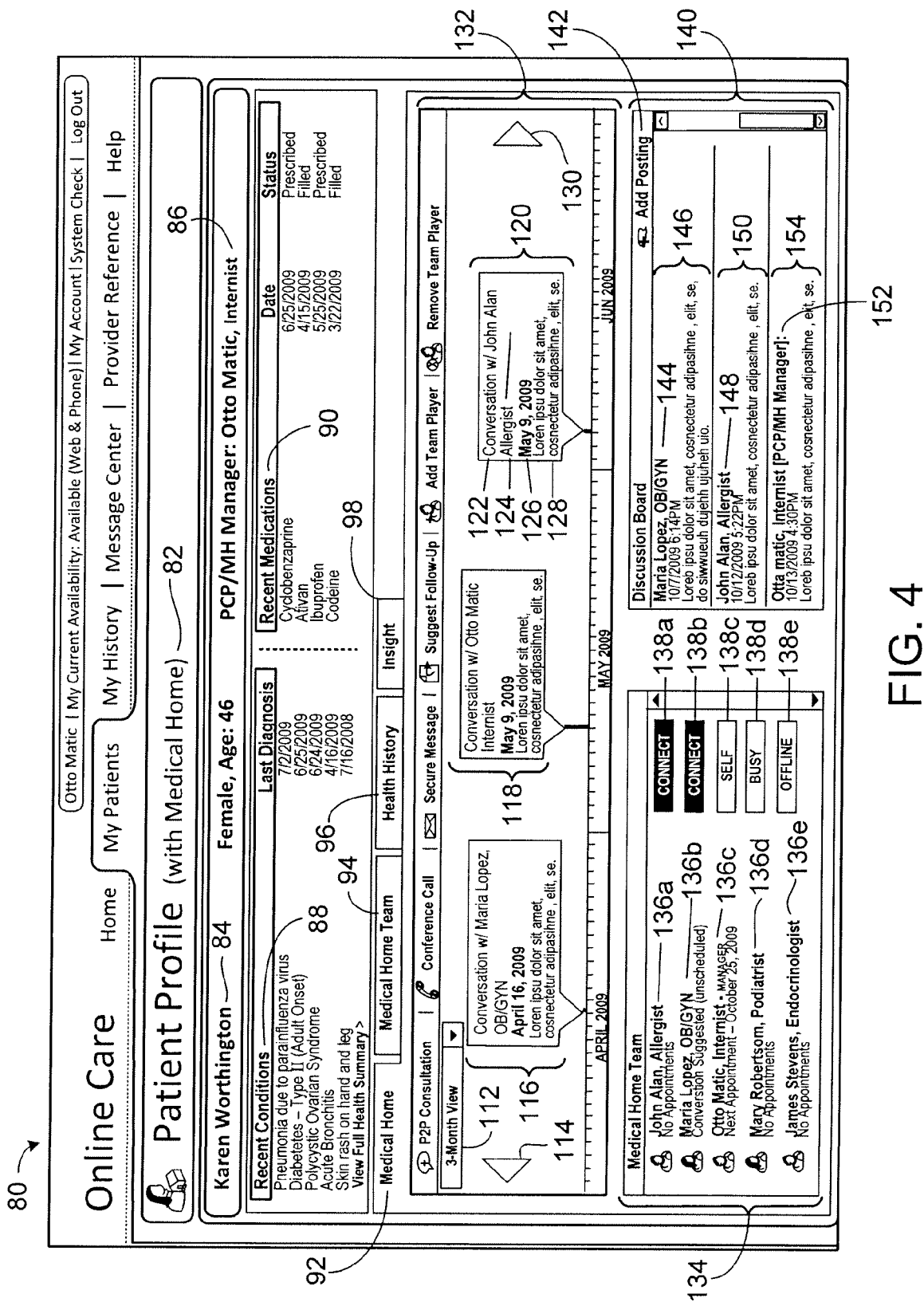

Referring to FIG. 4, the brokerage system 10 generates a graphical user interface 80 that includes details and links associated with a consumer's medical home team. The consumer's original profile graphical user interface 40 (FIG. 2) is updated, as shown, with text 82 indicating that the consumer 12 is associated with a medical home team. The graphical user interface 80 includes the name 84 of the consumer 12 for which the medical home team information is displayed. Section 86 of the graphical user interface 80 visually highlights the name of the medical home manager.

Section 88 of the graphical user interface 80 includes a list of supplemental information, including recent conditions. Section 90 of the graphical user interface 80 includes a list of recent medications associated with the consumer 12. The graphical user interface 80 also includes a section (not shown) through which a medical home team member adds notes regarding the consumer 12 and uploads files, such as medical history charts, associated with the consumer 12. When adding notes or files, the graphical user interface displays a prompt box in which the medical home team member specifies if the added notes and files are accessible and viewable by the consumer 12.

Tab or link 92 displays information associated with the consumer's medical home, as discussed in further detail below. Tab or link 94, when selected, displays information about the consumer's medical home team, as discussed in further detail below with regards to FIG. 9. Tab or link 96, when selected, displays information associated with a consumer's health history, as described in my issued patent, U.S. Pat. No. 7,590,550. Tab or link 98, when selected, displays decision support information. Decision support information gives providers real-time, evidence-based information and treatment recommendations for patients seen by the providers during online consultations.

The graphical user interface 80 includes a "P2P Consultation" link 100, selection of which initiates the establishment of a provider-to-provider consultation, as described in my co-pending U.S. patent application Ser. No. 12/614,842 filed on Nov. 9, 2009, the entire contents of which are incorporated herein by reference.

Through the "conference call" link 102, medical home team members initiate ("initiating medical home team member(s)") conference calls with other medical home team members, as discussed in further detail below, as discussed un further detail below with regards to FIG. 7.

Through a link 104 (e.g., the "secure message" link) medical home team members send secure messages to other medical home team members. The send secure message functionality allows a medical home team member to send a secure message to an individual medical home team member or to multiple medical home team members, such as all the service providers 14 included in the medical home team.

The graphical user interface 80 also includes a "suggest follow-up" link 106. By selecting the link 106, a medical home team member adds follow-up recommendations to a consumer's agenda, which is described in my issued patent, U.S. Pat. No. 7,590,550, or a list of items for the consumer 12 to perform. The types of follow-up actions added to a consumer's agenda or list include scheduling or engaging in a communication with a specific medical home team member, scheduling or engaging in a communication with a service provider 14 who is not a member of the consumer's medical home team, and participating in medical assessments, questionnaires and medical trackers to monitor and assess a consumer's health, such as a consumer's hemoglobin levels.

The medical home manager manages the medical home team by adding service providers 14 to the medical home team and removing service providers 14 from the medical home team. Graphical user interface 80 includes link 108, selection of which enables the medical home manager to add a service provider 14 to the medical home team. If the consumer's primary care physician is enrolled in the brokerage system 10, he/she is automatically added to the medical home team.

Graphical user interface 80 also includes link 110, selection of which enables the medical home manager to remove a service provider 14 from the medical home team. The brokerage system 10 generates a message and sends the message to the removed service provider 14 alerting the service provider 14 of the removal from the consumer's medical home team. Additionally, the brokerage system 10 generates a message and sends the message to the consumer 12 alerting the consumer 12 of the removal of the service provider 14 from the consumer's medical home team. Links 108, 110 displayed on the graphical user interface 80 are displayed for the medical home manager. Alternatively, links 108, 110 displayed on the graphical user interface 80 are displayed for the medical home manager and the medical home team members.

Still referring to FIG. 4, the graphical user interface 80 includes a timeline list 132 of the consumer's communications with the consumer's medical home team. A dropdown list 112 allows the medical home team member to select the time period, such as three months or twelve months, for which a consumer's communications are displayed. The timeline list 132 displays a visual representation 116, 118, 120 of the consumer's communications occurring during the selected time period. The displayed details include the name 122 and specialty 124 of the medical home team member engaging in the communication, the date 126 of the communication, and topics 128 discussed during the communication. The visual representation 116, 118, 120 of the consumer's communications is a link, selection of which causes another graphical user interface to display additional details, including topics discussed and diagnoses, of the communication between the medical home team member and the consumer 12. The timeline list 132 also includes links 114, 130, selection of which causes the time frame of the timeline list 132 to shift forwards or backwards, such as by forward or backward one month, and thus generate a new time frame and display a visual representation of the communications that occurred during the new time frame.

The graphical user interface 80 also includes a list 134 of active and invited medical home team members 136a-136e. A link is associated with each of the medical home team members 136a-136e, selection of which causes another graphical user interface to be displayed that includes, for the selected medical home team member, the medical home team member's name, specialty, patient star rating, gender, location, board certification, professional affiliations and education. For each medical home member 136a-136e, the current status 138a-138e, including busy, offline or available, of the medical home team member 136a-136e is displayed in graphical user interface 80. For the medical home team members 136a, 136b currently available, the medical home manager 136c (or medical home team member 136a-136e) is provided with the option of initiating a consultation with the available medical team member by selecting a link, including the "Connect" link 138a, 138b.

The discussion board section 140 of the graphical user interface 80 facilitates the medical home team members' 136a-136e discussion of and collaboration regarding a consumer 12. Through the selection of link 142, another graphical user interface (not shown) is displayed including textboxes in which a medical home team member 136a-136e posts a new item, such as a question or a diagnosis concerning the consumer 12, in the discussion board section 140 of the graphical user interface 80. The discussion board section 140 also includes visual representations 146, 150, 154 of prior postings made by medical home team members 136a-136e in the discussion board section 140. When a posting is added to the discussion board section 140, the brokerage system 10 captures and displays the "Date/Time Added" information and "Added by User" information and displays this information in the discussion board section 140 of the graphical user interface 80. Additionally, each posting includes the name and area of specialty 144, 148, 152 of the medical home team member 136a-136e making the posting. When a new message is added, the medical home team members 136a-136e, including the medical home manager 136c, receive a secure message indicating that a new posting has been made in the discussion board section 140.

The graphical user interface 80 may also include links or buttons (not shown) allowing the medical home manager to appoint a new medical home manager from the medical home team members 136a-136e. When the medical home manager 136c appoints a medical home team member 136a-136e to be the new medical home manager, a message is sent to the appointed medical home team member 136a-136e, informing the medical home team member 136a-136e of the appointment.

The graphical user interface 80 may include a link (not shown) through which a medical home team member 136a-136e exports or prints the list 134 of providers in the consumer's medical home team.

The brokerage system 10 also generates a graphical user interface through which medical home team members 136a-136e generate and edit distribution lists for members of the medical home team, with lists being selectable from a list of recipients when composing a secure message or replying to a secure message. The medical home team members 136a-136e communicate with one another in various other ways, including any combination of video conferencing, text chatting and talking to one another directly over a landline or voice-over internet protocol telephone connection facilitated and established through the brokerage system 10, as described in my co-pending U.S. patent application Ser. No. 12/105,784, published as "US-2009-0262919-A1," and incorporated herein by reference.

Graphical user interface 80 also includes a section with a textbox ("target textbox") (now shown) that is editable, in which a medical home team member 136a-136e sets target goals for the consumer 12. Each target textbox is associated with another text box ("status text box"), in which a medical home team member 136a-136e, including the medical home manager 136c, enters the status, such as "attained" or "incomplete," of each target goal. When a target goal is achieved, as indicated by a medical home team member 136a-136e editing the status text box to include "attained" text, the medical home team members 136a-136e receive a secure message indicating successful completion of the target goal. A list (not shown) of the completed target goals is visually displayed on the graphical user interface 80.

Figure 5:
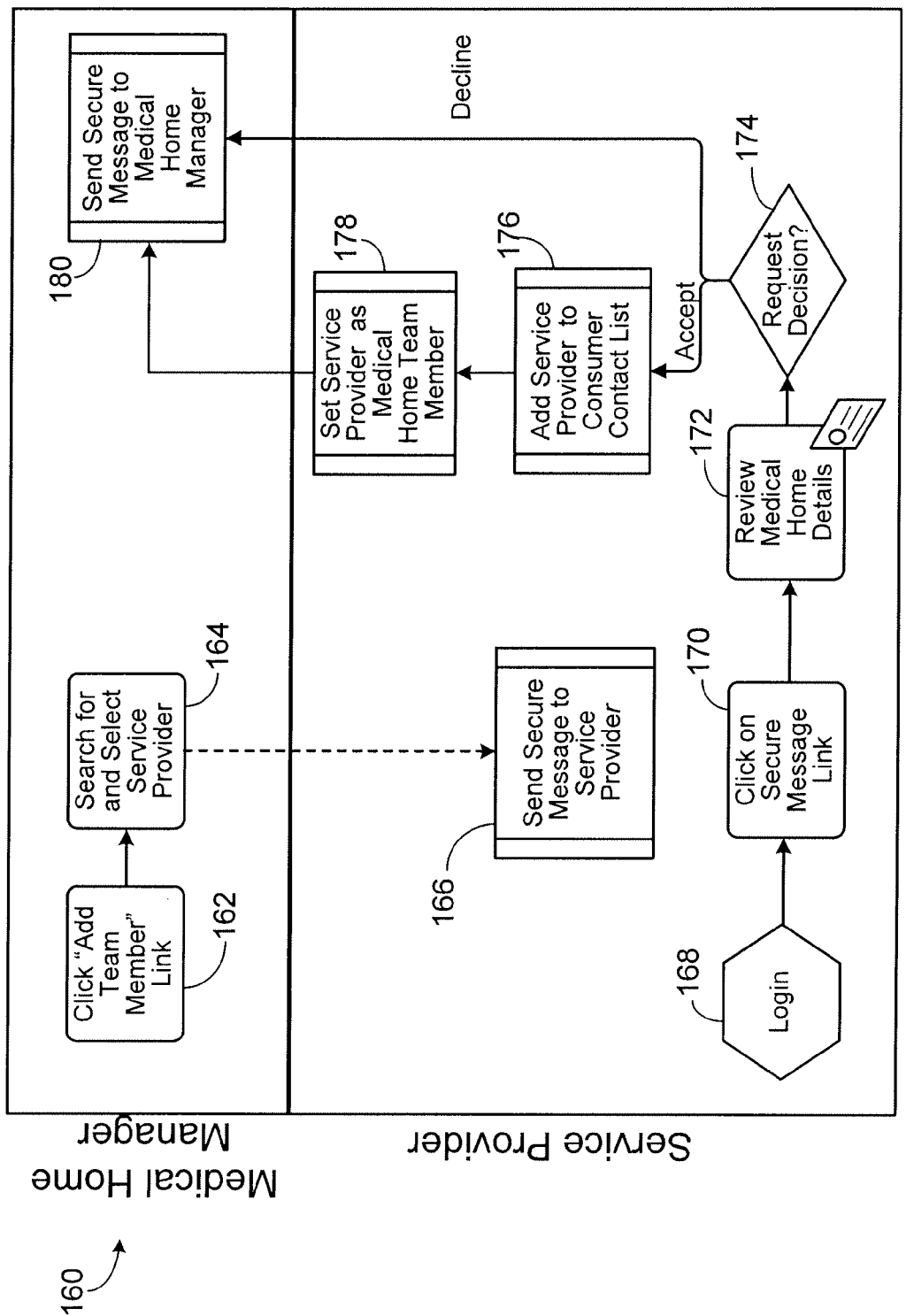

Referring to FIG. 5, the brokerage system 10 includes a computer server such as computer server 16 that adds 160 a service provider 14 to the medical home team, as follows. The medical home manger clicks 162 on the "add team member" link 108 (FIG. 4) and the brokerage system 10 generates and renders a graphical user interface that allows the medical home manager to search 164 and select a service provider 14 to add to the medical home team. The computer server (e.g., computer server 16) retrieves from a data repository records including names of one or more medical service providers that have provided medical services to a consumer of medical services. The medical home manager receives the results of these searches for service providers 14 to allow the medical home manager to add those service providers 14 to the medical home team, based on service provider name, service provider specialty or service provider area of practice.

The service provider 14 selected by the medical home manager to join the medical home team is sent 166 a secure message including an invitation to join the medical home team. The message can include a note that is added by the medical home manager that includes an explanation of why the medical home manager would like the service provider to join the medical home team. The invited service provider 14 accesses the secure message by logging 168 into the brokerage system 10 and clicking 170 on a link associated with the secure message, selection of the link causing the secure message to be displayed on a display device. The service provider 14 reviews 172 the secure message, including the invitation 208 (FIG. 6A) and determines 174 whether to accept or decline the invitation to join the medical home.

If the service provider 14 accepts the invitation, such as by selecting button 200 (FIG. 6A), the service provider 14 is added 176 to the consumer's contact list of service providers and the brokerage system 10 adds 178 the service provider 14 to the list 134 of medical home team members 136a-136e. A message is sent 180 to the medical home manager informing the medical home manager of the service provider's acceptance of the invitation. Additionally, the consumer 12 receives a secure message alerting the consumer 12 that the service provider 14 was added to the consumer's medical home team. If the service provider 14 declines the invitation, such as by selecting button 202 (FIG. 6A), a message is sent 180 to the medical home manager informing the medical home manager that the service provider 14 has declined the invitation.

Figure 6A:
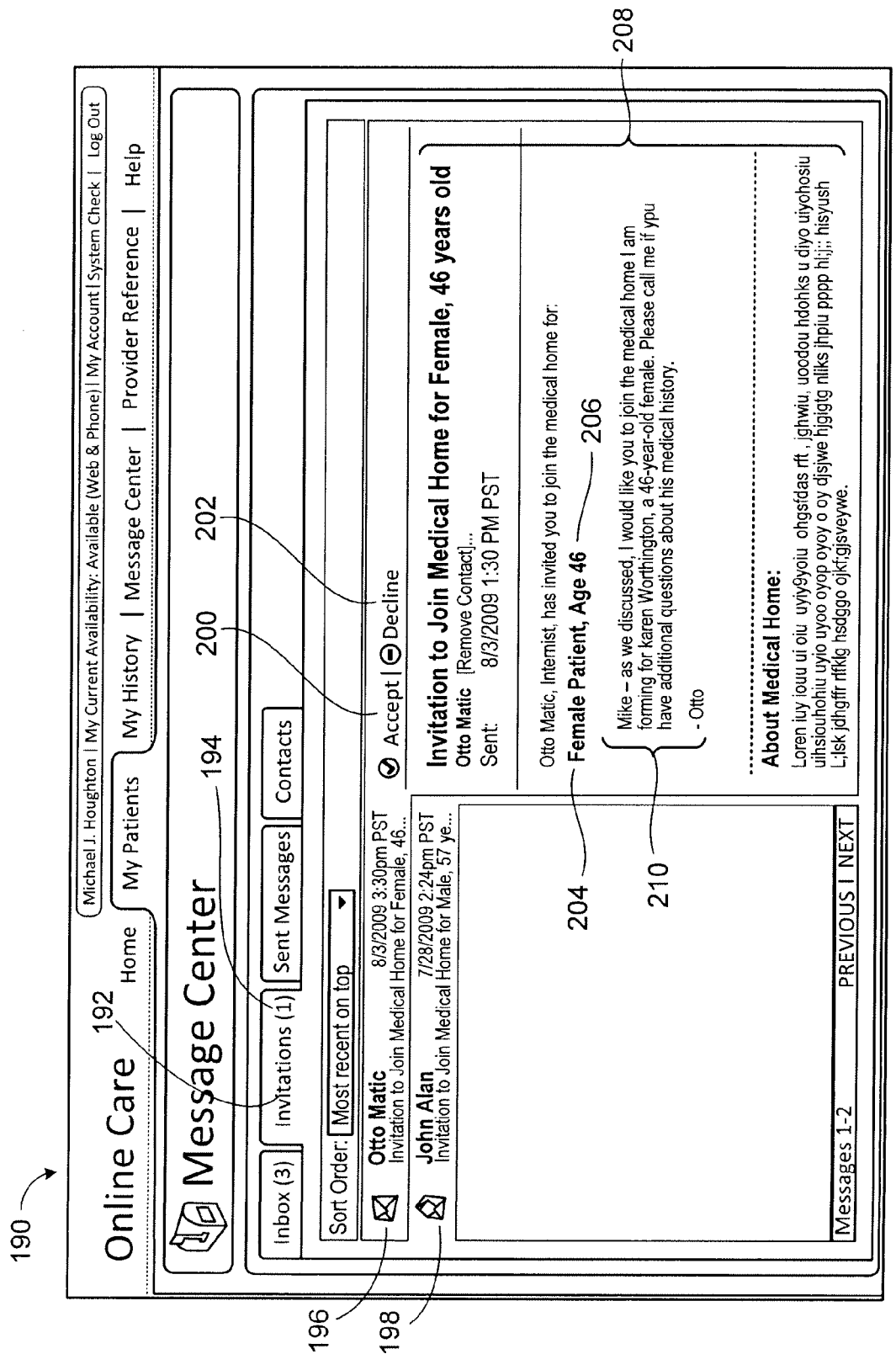

Referring to FIG. 6A, a graphical user interface 190 displays an invitations tab 192. The number of unread invitations 194 is displayed in the invitations tab 192. The invitations tab 192 also includes links 196, 198 associated with a service provider's invitations 208 to join a medical home team. By selecting one of the links 196, 198, the invitation 208 to join the medical home team is displayed by a display device, including client device 20 (FIG. 1).

The invitation 208 includes the gender 204 and age 206 of the consumer 12, along with a note 210 from the medical home manager. The graphical user interface 190 also includes an "accept" button 200, selection of which sends a message to the brokerage system 10 indicating that the service provider 14 accepts the invitation to join the medical home team. When accepting an invitation, the service provider 14 enters his/her initials certifying that a clinical relationship is being formed between the service provider 14 and the consumer 12. The graphical user interface 190 also includes a "decline" button 202, selection of which sends a message to the brokerage system 10 indicating that the service provider 14 declines the invitation to join the medical home team. When declining an invitation, a text box (not shown) is displayed in which the service provider 14 enters additional information pertaining to why the invitation was declined.

Referring to FIG. 6B, another graphical user interface 216 displays a message center section 218, including the number of unread invitations 220.

Figure 7:
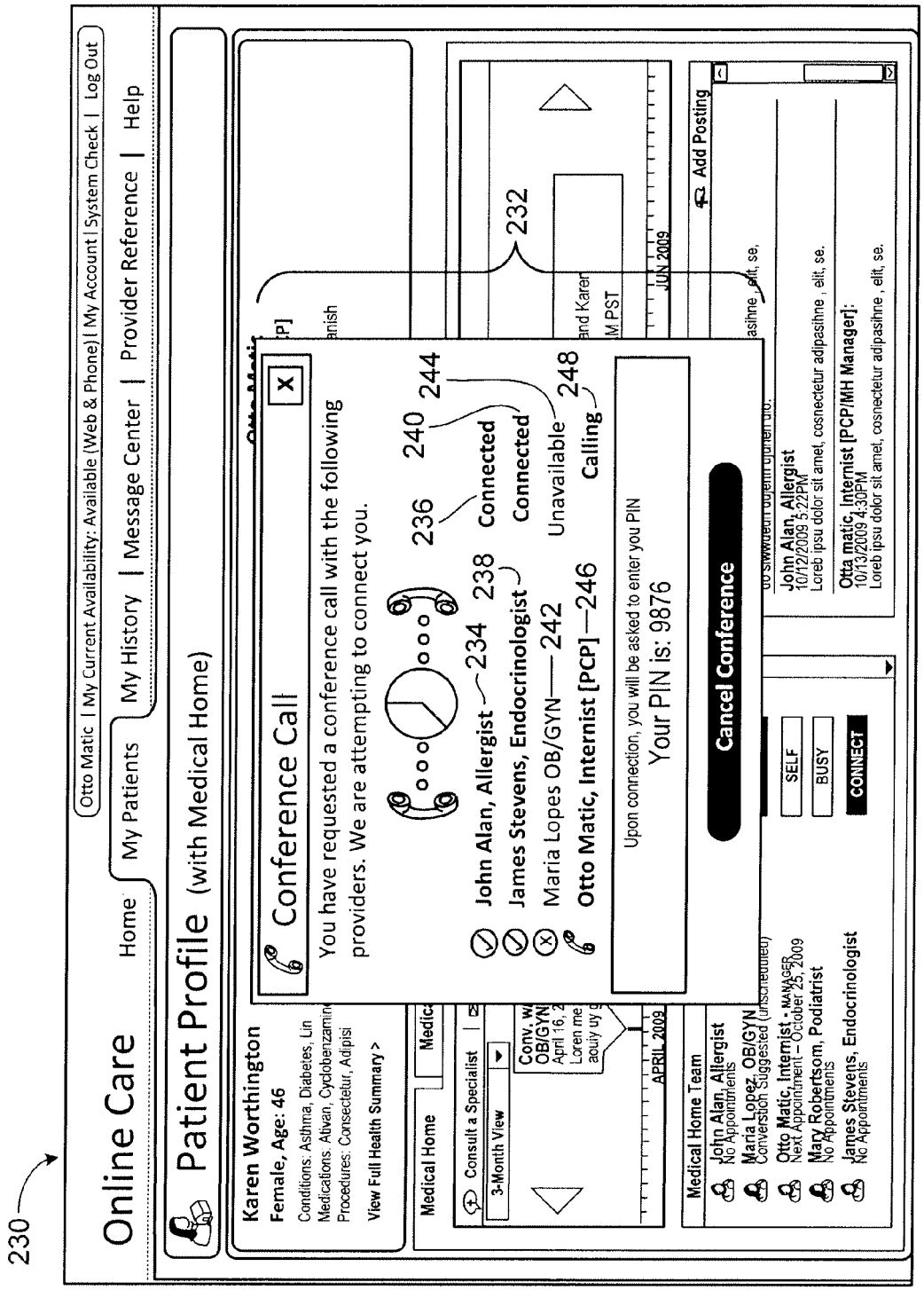

Referring now to FIG. 7, a graphical user interface 230 is generated when a medical home team member 136a-136e selects the conference call link 102 in FIG. 4. The initiating medical home team member selects one or more other medical home team members with whom to have a conference call. When the conference call is initiated, an intelligent voice response ("IVR") system initiates an outdial to the selected medical home team members. The IVR system indicates that this is a conference request from the initiating medical home team member on behalf of the consumer 12. The graphical user interface 230 includes a dialogue box 232 including details relating to a status of the conference call. The dialogue box 232 includes the names 234, 238, 242, 246 of the medical home team members 136a-136e requested to join the conference call by the initiating medical home team member 136a-136e. The dialogue box 232 also includes each medical home team member's progress and status in joining the conference call, including connected 236, 240, unavailable 244 and calling 248. Through selection of link 250, the initiating medical home team member 136a-136e cancels the conference call.

Referring to FIG. 8, a graphical user interface 260 includes a list 262 of a service provider's consumers 12. A relationship field 264, associated with each consumer 12, indicates the service provider's relationship, including medical home manager 266 and medical home team member 268, with the consumer 12. When a service provider 14 is added to a medical home team for a consumer 12, for example by accepting an invitation 208 (FIG. 6A) to join a medical home team, the brokerage system 10 updates the list 262 with the name of the consumer 12 for which the service provider 14 has been added to the consumer's medical home team and updates the relationship field 264 to indicate that the service provider 14 is a medical home team member 268 of the consumer's medical home team. When a service provider generates 52 (FIG. 3) a medical home team for a consumer 12, the relationship field 264 associated with the consumer 12 is updated to display in the graphical user interface 260 that the service provider 14 is the consumer's medical home manager 266.

Figure 9:
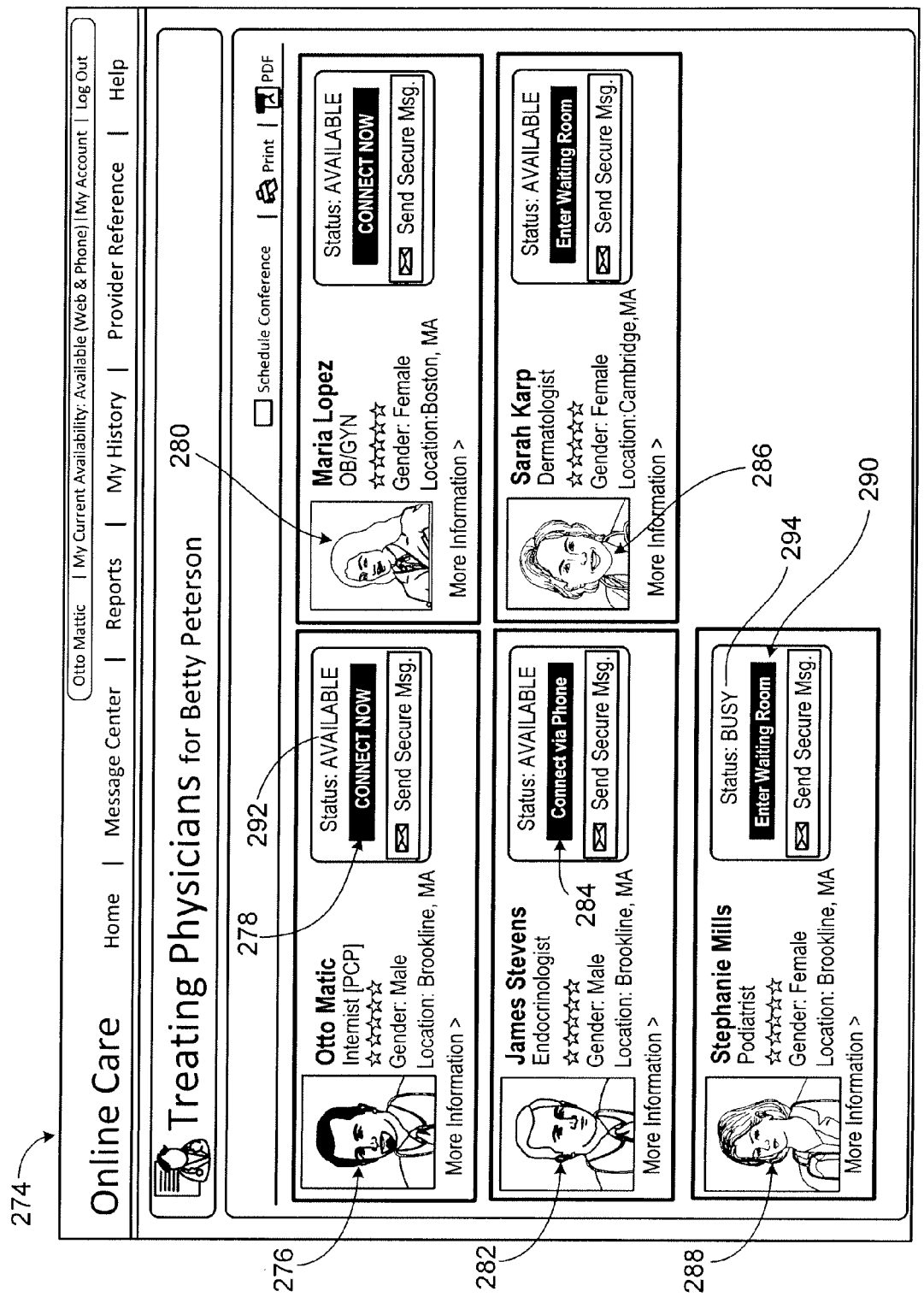

Referring to FIG. 9, a graphical user interface 274 is generated by the brokerage system 10 for display on a display device 18, 20. The graphical user interface 274 includes a visual representation of the medical home team members 276, 280, 282, 286, 288 associated with the consumer's medical home team. For each of the medical home team members 276, 280, 282, 286, 288, a status, including "available" 292 and "busy" 294, of the medical home team member 276, 280, 282, 286, 288 is displayed. For the available 292 medical home team members 276, 280, 282, 286, buttons 278, 284 are generated and displayed, selection of which initiates a communication between the consumer 12 and the available medical home team members 276, 280, 282, 286 associated with the selected button. Selection of button 290 places the consumer 12 in a virtual waiting room or queue until the medical home team member 286, 290 is available to engage in a communication with the consumer 12.

Figure 10:
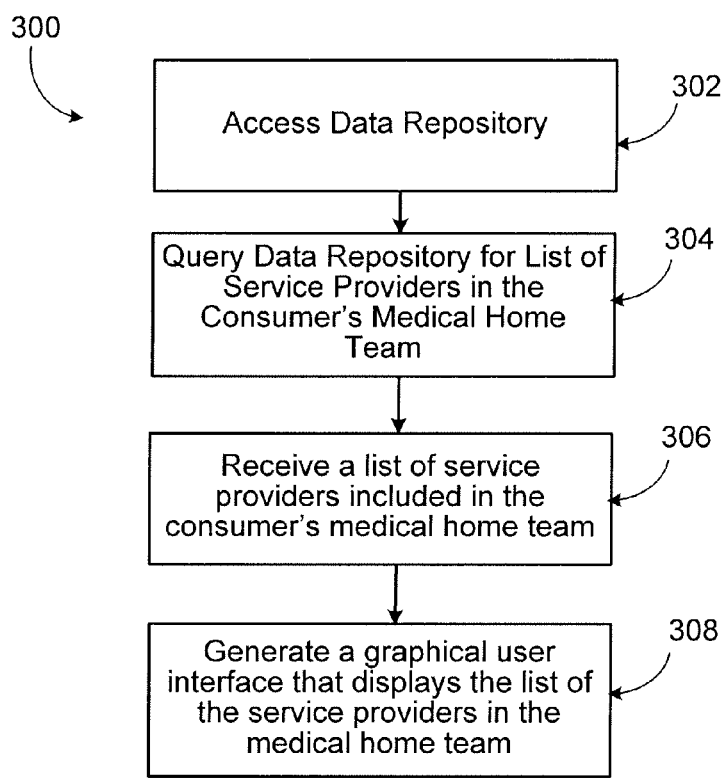

Referring to FIG. 10, various processes 300 are executed by the brokerage system 10 in generating the graphical user interface 274 (FIG. 9). The brokerage system 10 accesses 302 a data repository storing names of the medical home team members 136a-136e or 276, 280, 282, 286, 288 in a consumer's medical home team. The brokerage system 10 queries 304 the data repository for a list of the medical home team members 136a-136e (FIG. 4) and 276, 280, 282, 286, 288 (FIG. 9) associated with the consumer's medical home team. The brokerage system 10 receives 306 from the data repository a list of medical home team members 136a-136e and/or 276, 280, 282, 286, 288, included in the consumer's medical home team. Based on this list, the brokerage system 10 generates the graphical user interfaces 80 (FIG. 4) and/or 274 (FIG. 9) that displays a visual representation of the consumer's medical home team members 136c-136e and/or 276, 280, 282, 286, 288, respectively.

In generating graphical user interface 80, the brokerage system 10 also queries the database for supplemental information associated with the consumer of services 12, the name of the consumer's medical home manager, a list of prior communications the consumer 12 has engaged in with the consumer's medical home team members 136a-136e and a list of the prior postings made by medical home team members in the discussion board section 140 of the graphical user interface 80. Based on this information, the brokerage system 10 generates lists 88, 90 of supplemental information, the area 86 of the graphical user interface 80 which includes the name of the medical home manager, the timeline list 132 and the discussion board section 140 of the graphical user interface 80.

The medical home graphical user interface, including the graphical user interface 80, is generated and hosted by the same computing devices that host the brokerage system 10, as described in U.S. Pat. No. 7,590,550. The medical home graphical user interface is also generated and hosted by computing devices that are separate from the machines that host the brokerage system 10. The medical home graphical user interface is hosted on one computing device or more than one computing device in a distributed environment. The computing devices that host the medical home graphical user interface are connected to a data repository 34 that stores medical information for a consumer of medical services 12. The medical information includes the consumer's attending physicians and medical doctors, medical records, and medical prescriptions. When generating the medical home graphical user interface, the computing devices access and query the data repository for a consumer's medical information.

Embodiments can be implemented in digital electronic circuitry, or in computer hardware, firmware, software, or in combinations thereof Apparatus of the invention can be implemented in a computer program product tangibly embodied or stored in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

Other embodiments are within the scope and spirit of the description claims. In one example, the brokerage system 10 is used to generate a graphical user interface through which various types of service providers 14, including legal service providers (e.g., attorneys and paralegals) and financial service providers (e.g., accounts and fund managers), collaborate and share information pertaining to a client. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A computer-implemented method comprises:
receiving, by a computer, a request to generate a medical service team for a particular consumer of medical services;
accessing by the computer a data repository storing records of medical service providers providing a medical service to the consumer of medical services;
sending by the computer an electronic message to the medical service providers corresponding to the retrieved records, the electronic message including an invitation to join the medical service team associated with providing medical services to the consumer of medical services;
receiving by the computer responses to the electronic message; and generating from the responses and the records a listing of medical service team members in the medical service team, with the medical service team members providing the medical service to the consumer of medical services;

receiving, by the computer, a request to view information representing medical service providers who are associated with attributes specifying that the medical service providers are medical service team members of the medical service team of the consumer;

accessing, by the computer, a data repository that stores information pertaining to medical service providers, including availability of the medical service providers for participating in a consultation;

determining in the computer, which of the medical service providers are available;

identifying in the computer, an available medical service provider associated with one or more attributes that specify that the available medical service provider is a medical service team member of the medical service team of the consumer; and producing information indicative of the available medical service team member.

2. The computer-implemented method of claim 1 further comprising:

receiving, from one of the medical service team members, an instruction to send the electronic message to one or more selected service providers.

3. The computer-implemented method of claim 1 further comprising:

updating the listing of medical service team members with names of one or more service providers accepting the electronic message;

wherein the computer assembles the medical service team at least in part by identifying, from the accessed records, those service providers that are collaborating together to provide the consumer with coordinated health care, and with the computer further configured to allow the medical service team members to share clinical information regarding the consumer, to view updates to a consumer's health record and to initiate consultations with each other or other service providers.

4. The computer-implemented method of claim 1 further comprising:

receiving, from one of the medical service team members, a message including names of one or more other medical service team members to be removed from the listing of medical service team members; and removing, from the listing of medical service team members, the received names of the one or more other medical service team members.

5. The computer-implemented method of claim 1 further comprising:

retrieving from a data repository status data regarding availability of the one or more medical service providers on the listing of medical service team members; and generating data for a user interface that renders one or more visual representations of the one or more medical service providers with an indication of the availability status of the one or more medical service providers juxtaposed to the one or more visual representations.

6. The computer-implemented method of claim 1 further comprising:

retrieving from a data repository medical specialty data of the one or more medical service providers on the listing of medical service team members; and generating a user interface that renders one or more visual representations of the one or more medical service providers with medical specialty data of the medical service providers juxtaposed to the one or more visual representations.

7. The computer-implemented method of claim 1 further comprising:

establishing a real-time communication channel between a device used by one of the medical service team members and a device used by one or more other, different medical service team members.

8. The computer-implemented method of claim 1 further comprising:

establishing a real-time communication channel between a device used by one or more of the medical service team members and a device used by the consumer of medical services.

9. A computer program product tangibly embodied on a computer readable storage device, the computer program product comprising instructions for causing a computer to:

receive a request to generate a medical service team for a particular consumer of medical services;

access the data repository storing records of one or more medical service providers providing a medical service to the consumer of medical services;

send an electronic message to medical service providers corresponding to the retrieved records, the electronic message including an invitation to join the medical service team associated with providing medical services to the consumer of medical services;

receive responses to the electronic message;

generate from the responses and the records a listing of medical service team members in the medical service team, with the medical service team members providing the medical service to the consumer of medical services;

receive a request to view information representing medical service providers who are associated with attributes specifying that the medical service providers are medical service team members of the medical service team of the consumer;

access a data repository that stores information pertaining to medical service providers, including availability of the medical service providers for participating in a consultation;

determine which of the medical service providers are available;

identify an available medical service provider associated with one or more attributes that specify that the available medical service provider is a medical service team member of the medical service team of the consumer; and produce information indicative of the available medical service team member.

10. The computer program product of claim 9 further comprising instructions for causing the computer to:

update the listing of medical service team members with names of one or more service providers accepting the electronic message;

wherein the computer assembles the medical service team at least in part by identifying, from the accessed records, those service providers that are collaborating together to provide the consumer with coordinated health care, and with the computer further configured to allow the medical service team members to share clinical information regarding the consumer, to view updates to a consumer's health record and to initiate consultations with each other or other service providers.

11. The computer program product of claim 9 further comprising instructions for causing the computer to:

receive, from one of the medical service team members, a message including names of one or more other medical service team members to be removed from the listing of medical service team members; and remove, from the listing of medical service team members, the received names of the one or more other medical service team members.

12. The computer program product of claim 9 further comprising instructions for causing the computer to:

retrieve from a data repository status data regarding availability of the one or more medical service providers on the listing of medical service team members; and generate data for a user interface that renders one or more visual representations of the one or more medical service providers with an indication of the availability status of the one or more medical service providers juxtaposed to the one or more visual representations.

13. An apparatus comprising:

a processor; and a computer program product residing on a computer readable medium, the computer program product comprising instructions for causing the processor to:

receive a request to generate a medical service team for a particular consumer of medical services;

access a data repository storing records of one or more medical service providers providing a medical service to the consumer of medical services;

send an electronic message to medical service providers corresponding to the retrieved records, the electronic message including an invitation to join the medical service team associated with providing medical services to the consumer of medical services;

receive responses to the electronic message; and generate from the responses and the records a listing of medical service team members in the medical service team, with the medical service team members providing the medical service to the consumer of medical services;

receive a request to view information representing medical service providers who are associated with attributes specifying that the medical service providers are medical service team members of the medical service team of the consumer;

access a data repository that stores information pertaining to medical service providers, including availability of the medical service providers for participating in a consultation;

determine which of the medical service providers are available;

identify an available medical service provider associated with one or more attributes that specify that the available medical service provider is a medical service team member of the medical service team of the consumer; and produce information indicative of the available medical service team member.

14. The apparatus of claim 13, the computer program product further comprising instructions to:

update the listing of medical service team members with names of one or more service providers accepting the electronic message;

wherein the processor assembles the medical service team at least in part by identifying, from the accessed records, those service providers that are collaborating together to provide the consumer with coordinated health care, and with the computer further configured to allow the medical service team members to share clinical information regarding the consumer, to view updates to a consumer's health record and to initiate consultations with each other or other service providers.

15. The apparatus of claim 13, the computer program product further comprising instructions to:

receive, from one of the medical service team members, a message including names of one or more other medical service team members to be removed from the listing of medical service team members; and remove, from the listing of medical service team members, the received names of the one or more other medical service team members.

16. The apparatus of claim 13, the computer program product further comprising instructions to:

retrieve from a data repository status data regarding availability of the one or more medical service providers on the listing of medical service team members; and generate data for a user interface that renders one or more visual representations of the one or more medical service providers with an indication of the availability status of the one or more medical service providers juxtaposed to the one or more visual representations.

17. A computer-implemented method comprising:

retrieving, by a computer, records from a data repository, with the records specifying names of medical service providers providing a medical service to a consumer;

generating data for a user interface that comprises:

an invitation link, for at least one of the medical service providers corresponding to the retrieved records, to join a medical service team for the consumer of medical services; and one or more messages associated with the invitation link to join the medical service team for the consumer of medical services;

wherein the computer assembles the medical service team at least in part by identifying, from the accessed records, those service providers that are collaborating together to provide the consumer with coordinated health care, and with the computer further configured to allow the medical service team members to share clinical information regarding the consumer, to view updates to a consumer's health record and to initiate consultations with each other or other service providers;

receiving, by the computer, a request to view information representing medical service providers who are associated with attributes specifying that the medical service providers are medical service team members of the medical service team of the consumer;

accessing, by the computer, a data repository that stores information pertaining to medical service providers, including availability of the medical service providers for participating in a consultation;

determining in the computer, which of the medical service providers are available;

identifying in the computer, an available medical service provider associated with one or more attributes that specify that the available medical service provider is a medical service team member of the medical service team of the consumer; and producing information indicative of the available medical service team member.

18. The computer-implemented method of claim 17, further comprising:

generating data for a second user interface that displays a listing of members of the medical service team and names of one or more medical service providers accepting the invitation.

19. The computer-implemented method of claim 17, wherein the user interface is a first user interface, the method further comprising:
generating data for a second user interface that renders one or more visual representations of one or more medical service providers in the medical service team, with an indication of availability status of the one or more medical service providers juxtaposed to the one or more visual representations.

20. The computer-implemented method of claim 17 further comprising:
generating data for the user interface with a link that corresponds to a request for a real-time communication with a member of the medical service team.

21. A computer program product tangibly embodied on a computer readable storage device, the computer program product comprising instructions for causing a computer to:
retrieve records from a data repository, with the retrieved records specifying names of medical service providers providing a medical service to a consumer;
generate data for a user interface that comprises:
an invitation link, for at least one of the medical service providers corresponding to the retrieved records, to join a medical service team for the consumer of medical services; and
one or more messages associated with the invitation link to join the medical service team for the consumer of medical services;
wherein the computer assembles the medical service team at least in part by identifying, from the accessed records, those service providers that are collaborating together to provide the consumer with coordinated health care, and with the computer further configured to allow the medical service team members to share clinical information regarding the consumer, to view updates to a consumer's health record and to initiate consultations with each other or other service providers;
receive a request to view information representing medical service providers who are associated with attributes specifying that the medical service providers are medical service team members of the medical service team of the consumer;
access a data repository that stores information pertaining to medical service providers, including availability of the medical service providers for participating in a consultation;
determine which of the medical service providers are available;
identify an available medical service provider associated with one or more attributes that specify that the available medical service provider is a medical service team member of the medical service team of the consumer; and
produce information indicative of the available medical service team member.

22. An apparatus comprising:
a processor; and
a computer program product residing on a computer readable medium, the computer program product comprising instructions for causing the processor to:
retrieve records from a data repository, with the retrieved records specifying names of medical service providers providing a medical service to a consumer;
generate data for a user interface that comprises:
an invitation link, for at least one of the medical service providers corresponding to the retrieved records, to join a medical service team for the consumer of medical services; and
one or more messages associated with the invitation link to join the medical service team for the consumer of medical services;
wherein the computer assembles the medical service team at least in part by identifying, from the accessed records, those service providers that are collaborating together to provide the consumer with coordinated health care, and with the computer further configured to allow the medical service team members to share clinical information regarding the consumer, to view updates to a consumer's health record and to initiate consultations with each other or other service providers;
receive a request to view information representing medical service providers who are associated with attributes specifying that the medical service providers are medical service team members of the medical service team of the consumer;
access a data repository that stores information pertaining to medical service providers, including availability of the medical service providers for participating in a consultation;
determine which of the medical service providers are available;
identify an available medical service provider associated with one or more attributes that specify that the available medical service provider is a medical service team member of the medical service team of the consumer; and
produce information indicative of the available medical service team member.

23. The computer program product of claim 9 further comprising instructions for causing the computer to:
retrieve from a data repository medical specialty data of the one or more medical service providers on the listing of medical service team members; and
generate a user interface that renders one or more visual representations of the one or more medical service providers with medical specialty data of the medical service providers juxtaposed to the one or more visual representations.

24. The computer program product of claim 9 further comprising instructions for causing the computer to:
establish a real-time communication channel between a device used by one of the medical service team members and a device used by one or more other, different medical service team members.

25. The computer program product of claim 9 further comprising instructions for causing the computer to:
establish a real-time communication channel between a device used by one or more of the medical service team members and a device used by the consumer of medical services.

26. The apparatus of claim 13, the computer program product further comprising instructions to:
retrieve from a data repository medical specialty data of the one or more medical service providers on the listing of medical service team members; and
generate a user interface that renders one or more visual representations of the one or more medical service providers with medical specialty data of the medical service providers juxtaposed to the one or more visual representations.

27. The apparatus of claim 13, the computer program product further comprising instructions to:

establish a real-time communication channel between a device used by one of the medical service team members and a device used by one or more other, different medical service team members.

28. The apparatus of claim 13, the computer program product further comprising instructions to:
establish a real-time communication channel between a device used by one or more of the medical service team members and a device used by the consumer of medical services.

29. The computer program product of claim 21, wherein the user interface is a first user interface, and wherein the computer program product further comprises instructions for causing the computer to:
generate data for a second user interface that renders one or more visual representations of one or more medical service providers in the medical service team, with an indication of availability status of the one or more medical service providers juxtaposed to the one or more visual representations.

30. The computer program product of claim 21, further comprising instructions for causing the computer to:
generate data for the user interface with a link that corresponds to a request for a real-time communication with a member of the medical service team.

31. The apparatus of claim 22, wherein the user interface is a first user interface, and wherein the computer program product further comprises instructions for causing the computer to:
generate data for a second user interface that renders one or more visual representations of one or more medical service providers in the medical service team, with an indication of availability status of the one or more medical service providers juxtaposed to the one or more visual representations.

32. The apparatus of claim 22, wherein the computer program product further comprises instructions for causing the computer to:
generate data for the user interface with a link that corresponds to a request for a real-time communication with a member of the medical service team.

* * * * *